(12) United States Patent
Gleba et al.

(10) Patent No.: US 7,670,801 B2
(45) Date of Patent: Mar. 2, 2010

(54) USING VIRUSES TO DETECT OR PURIFY PROTEINS

(75) Inventors: Yuri Gleba, München (DE); Newell Bascomb, Wayne, NJ (US); Valentin Negrouk, Plainsboro, NJ (US)

(73) Assignee: Icon Genetics, Inc., Princeton, NJ (US)

( * ) Notice: Subject to any disclaimer, the term of this patent is extended or adjusted under 35 U.S.C. 154(b) by 888 days.

(21) Appl. No.: 10/466,291

(22) PCT Filed: Jan. 18, 2002

(86) PCT No.: PCT/US02/01676

§ 371 (c)(1),
(2), (4) Date: Jul. 15, 2003

(87) PCT Pub. No.: WO02/068927

PCT Pub. Date: Sep. 6, 2002

(65) Prior Publication Data

US 2004/0214160 A1 Oct. 28, 2004

Related U.S. Application Data

(60) Provisional application No. 60/262,466, filed on Jan. 18, 2001.

(51) Int. Cl.
| | |
|---|---|
| C12N 15/09 | (2006.01) |
| C12N 7/01 | (2006.01) |
| C12N 7/02 | (2006.01) |
| C12N 7/00 | (2006.01) |
| C07K 1/36 | (2006.01) |

(52) U.S. Cl. .................. 435/69.1; 435/419; 435/235.1; 435/239; 530/412; 530/413

(58) Field of Classification Search ............... 435/69.1, 435/235.1, 419; 530/412, 413
See application file for complete search history.

(56) References Cited

U.S. PATENT DOCUMENTS

| | | | | |
|---|---|---|---|---|
| 4,459,359 | A | * | 7/1984 | Neurath .......................... 435/5 |
| 5,955,341 | A | | 9/1999 | Kang et al. |
| 6,825,325 | B1 | * | 11/2004 | Fischer et al. ............ 530/388.2 |

FOREIGN PATENT DOCUMENTS

| | | |
|---|---|---|
| WO | WO-97/44491 A1 | 11/1997 |
| WO | WO-99/46288 | 9/1999 |

OTHER PUBLICATIONS

Turpen. Phil. Trans. R. Soc. Lond. B 354:665-673, 1999.*
Pereira, S. et al., A model system for detection and isolation of a tumor cell surface antigen using antibody phage display, Journal of Immunological Methods, vol. 203, Issue 1, Apr. 11, 1997, pp. 11-24.*
Turpen, T., Tobacco mosaic virus and the virescence of biotechnology.Philos Trans R Soc Lond B Biol Sci. 1999 vol. 354(1383), pp. 665-673.*
Smith, et al., "Cross-linked filamentous phage as an affinity matrix", Journal of Immunological Methods, vol. 215, pp. 151-161, 1998.
Joelson, et al., "Presentation of a foreign peptide on the surface of tomato bushy stunt virus", Journal of General Virology, vol. 78, pp. 1213-1217, 1997.
Smolenska, et al., "Production of a functional single chain antibody attached to the surface of a plant virus", FEBS letters, vol. 441, pp. 379-382, 1998.
Poon, et al., "Phage-displayed La/SS-B antigen as a diagnostic reagent", Immunotechnology, vol. 3, pp. 155-159, 1997.
Crosby, et al., "Principles and Application of Recombinant Antibody Phage Display Technology to Plant Biology", Methods In Cell Biology, vol. 50, pp. 85-99, 1995.
Prezzi, et al., "Selection of Antigenic and Immunogenic Mimics of Hepatitis C Virus Using Sera from Patients", Journal of Immunology, vol. 156, pp. 4504-4513, 1996.
Reed B. Wickner, "Yeast virology", FASEB Journal, vol. 3, pp. 2256-2265, 1989.
Ehsani, P. et al.; Polypeptides of Hepatitis B Surface Antigen Produced in Transgenic Potato, *Gene*; 1997, pp. 107-111:190, Elsevier Science B.V.
Mejàre, M. et al.; Evaluation of Genetically Attached Histidine Affinity Tails for Purification of Lactate Dehydrogenase From Transgenic Tobacco, *Plant Science*, 1998, pp. 103-114:134, Elsevier Science B.V.

* cited by examiner

*Primary Examiner*—Mary E Mosher
*Assistant Examiner*—Myron G Hill
(74) *Attorney, Agent, or Firm*—Lerner, David, Littenberg, Krumholz & Mentlik, LLP (57) ABSTRACT

Disclosed are methods of isolating and purifying proteins and other organic small molecules produced in hosts using viruses. Also disclosed are methods of visualizing and/or localizing proteins and other organic small molecules produced in hosts using viruses. Further disclosed are compositions of matter containing the protein or small molecule bound to a virus.

27 Claims, 3 Drawing Sheets

STR>

1    2    3

USING VIRUSES TO DETECT OR PURIFY PROTEINS

CROSS-REFERENCE TO RELATED APPLICATIONS

This application is a national stage entry under 35 U.S.C. §371 of International Application Number PCT/US02/01676, filed Jan. 18, 2002, which claims the benefit of U.S. Application No. 60/262,466, filed Jan. 18, 2001.

TECHNICAL FIELD

The present invention relates to the use of viruses to detect or isolate proteins and small molecules from hosts in which they are produced.

BACKGROUND ART

During the last several years, significant progress was made in utilization of transgenic plants and other living organisms for production of industrial oils, plastics, edible vaccines and industrially important recombinant proteins. In two latter cases, it was found that plants are able to produce high levels of safe, functional, recombinant proteins and can be easily expanded to agricultural levels to meet industrial demands (Fischer et al., 1999 a, b). Current applications of plants, microorganisms and animal cells in biotechnology include the production of hormones, enzymes, antibodies, plasma proteins, cytokines and vaccines. Recombinant proteins can be produced either by genetically inherited expression in transgenic plants or by transient expression in virus-infected plants.

A revolutionary breakthrough in large-scale production of recombinant proteins in plants was made several years ago by using plant RNA viruses (Kumagai et al., 1993; Hamamoto et al., 1993). The principle of all RNA viral expression systems is the same: upon inoculation, viral RNA replicates in the cytoplasm to high copy number, and the viral progeny RNA is translated resulting in the expression of virally encoded proteins. The virus moves systemically through the whole plant by cell-to-cell and long-distance movement. For vector construction, viral RNA genomes are reverse-transcribed in vitro and cloned as full-length cDNAs in transcription vectors in vitro or in vivo (Boyer, Haenni, 1994). The cloned viral genomes can then be manipulated with standard DNA techniques. For inoculation of plants, recombinant viral vectors are usually transcribed in vitro and the synthesized RNA is inoculated mechanically onto plants by gently rubbing the leaves with a mild abrasive. Extracts from these infected plants can also be used for the subsequent inoculation of very large numbers of plants. One of the most efficient transient expression viral vectors is tobacco mosaic virus (TMV)-based hybrid vectors that contain a heterologous coat protein subgenomic mRNA promoter and coat protein open reading frame and either TMV or heterologous 3' non-translated region (Shivprasad et al, 1999). The size of the gene that can be expressed with viral vector usually does not exceed 2 kb.

A comparison of features of recombinant protein production in plants, yeast, bacterial, and animal systems is presented in Fischer et al, (1999 a, b). Both transgenic plants and plant viral systems have many advantages compared to the yeast, bacterial, and animal systems. One of the most impressive advantages of the recombinant protein production in plants is the cost of production. The production of proteins from plants infected with viral vectors is several times lower compared to stable transformed transgenic plants. In addition, the time required for the creation of a new plant viral vector product is significantly lower compared to transgenic plants. This low cost and high speed turnaround time are especially important for biotechnological companies. According to data presented by Large Scale Biology (formerly Biosource), the time required to go from a gene expression feasibility study to greenhouse and/or pilot field production, to recovery and purification into purified protein product takes about a year. For transgenic plants it would take at least three years under ideal circumstances. Viral RNA vector systems can be used for the production of different proteins and polypeptides ranging in mass from 4 kd to about 70 kd.

Small epitopic oligopeptides (e.g., less than 25 amino acids in length) can also be produced on the surface of viral particles by gene-fusions created with coat-protein genes (Hamamoto et al., 1993; Fitchen et al., 1995; McLain et al., 1995; Yusibov et al., 1997; Johnson et al., 1997; Koo et al., 1999). There are significant data demonstrating that epitopic oligopeptides on the surface of TMV or other plant viruses induce a strong immune response in vaccinated animals.

On the other hand, for proteins or molecules requiring a high degree of purity, downstream processing from plant biomass is assumed to be generally more problematic and expensive. As a rule, the recombinant product constitutes only a minor fraction of the total biomass. It is well known that in microbial production systems that have been optimized with regard to product yield, up to 90% of total production costs are the costs related to purification of the molecule of interest from the host, rather than expenses of the production itself To make the production from transgenic plants economical, strategies are needed that will allow rapid and inexpensive separation of the recombinant or endogenous proteins of interest or non-proteinaceous small molecules, from other endogenous plant molecules. Since most efficient purification platforms are based on specific affinity between the molecule of interest and the purification matrix, the problem is best addressed by developing a simple and inexpensive high-affinity matrix that can than be used to specifically bind the molecule of interest. One such matrix contemplated in this invention is a protein surface of a virus particle.

The size and biochemical characteristics of every protein are different, so the method of purification must be different for different proteins. One of the approaches that would have a general applicability is the use of separation techniques to concentrate and purify the protein by affinity-mediated isolation. As in microbial systems, expression of the proteins as fusion products (i.e., having an affinity tag) would also facilitate the use of affinity isolation for recovery from plant extracts. There are a number of different commercially available fusion tags for bacterial and animal systems. At least some of them might work in plants; however, they are too expensive for large-scale production.

Ideal characteristics of an ideal affinity tag-based purification system include a homogenous, inexpensive, uniform and specific molecular surface which itself can form large stable aggregates with mass significantly greater than 200-300 kd. This aggregate should bear affinity tags on its surface strong enough to be bound by the protein of interest and to purify it by precipitation. The complex with the protein of interest should in turn, be easy to dissociate under relatively mild ionic conditions. Ideally the affinity matrix would be reusable. Such a system could be used not only in plant biotechnology but also for protein purification in bacterial and animal biotechnology.

SUMMARY OF THE INVENTION

Applicants have invented methods for the purification or visualization of proteins or small molecules using viruses. The method is applicable to a wide variety of protein expression systems including plants, animals and bacteria.

A first aspect of the present invention is directed to a method of purifying a protein or non-proteinaceous small molecule of interest. The method entails: (a) providing a virus having on its surface at least one recognition peptide. The recognition peptide may be present as a sub-sequence on the surface of (one of) the viral coat protein(s). Alternatively, a viral expression vector is provided, wherein the vector will direct re-assembly of particles of the virus in an organism or cells thereof (e.g., the host). The method also involves (b) obtaining a host that produces the protein or small molecule of interest independent from or due to presence of the virus therein. The protein or small molecule may be produced endogenously by the host or exogenously as a result of the presence of one or more transgenes introduced into the host by way the viral expression vector or via a transformation event with a distinct nucleic acid vector. The virus is caused to come into contact with the protein or small molecule in order to bind (e.g., form a complex) therewith. This can be achieved by infecting the host with the virus or the viral expression vector, followed by harvesting the complexes of the virus and protein from the host. Alternatively, a lysate of the host or another type of solution (e.g., homogenate) of the host (and which contains the protein) may be prepared. The protein can be isolated from the solution by contacting the solution with the virus e.g., absorbed on an affinity matrix such as a column. The binding of the virus with the protein or small molecule may be direct or indirect in the sense that the virus may have affinity for the protein per se, or for a fusion partner that is co-expressed with the protein. The recognition peptide may be endogenous to the virus (i.e., present in a naturally occurring wild-type or mutant) virus or can be the result of a genetic modification to a virus whereby an affinity or recognition peptide is integrated into a surface of a coat protein of the virus. The virus particles having the protein or small molecule of interest bound thereto are harvested, whereupon the virus and protein may be dissociated from one another.

In various preferred embodiments, the host is a transgenic plant such as *nicotiana, brassica, arabidopsis,* soybean, wheat, pearl millet or maize; the virus is tobacco mosaic virus (TMV), Bean Golden Mosaic Virus, an adenovirus, baculovirus or a phage e.g., T even and T odd phage; the protein is expressed in the form of a fusion protein, and the cleavable linkage between the protein and its fusion partner is an enterokinase or cyanogen bromide site; and the virus and fusion protein are brought into contact by infecting the plant with a vector containing the viral nucleic acid (e.g., a plant, animal, bacterial or yeast viral vector). The fusion partner, which is a peptide having affinity for a recognition sequence on a virus, is a single chain fragment of an antibody or an antibody, and the recognition sequence is non-native to the virus such as a polyhistidine or a FLAG peptide. Hence, a preferred embodiment in accordance with this aspect of the present invention is directed to method of production and purification of an exogenous protein produced in a plant host. The method involves (a) providing a plant virus containing a coat protein, wherein a surface of the coat protein contains a recognition peptide (more preferably one which is non-native to the virus), or in the alternative providing a (recombinant) viral expression vector or pro-vector which upon expression in a cell of the plant host yields particles of the virus. The host is genetically modified with one or more transgenes to produce the protein of interest (and more preferably to produce the protein in the form of a fusion wherein the peptide linked to the protein binds the recognition peptide on the viral surface. The virus particles are caused to come into contact with the protein. This contact is achieved by infecting the host with the virus, introducing the viral expression vector into the host followed by harvesting the complexes of virus and protein from the host. Alternatively, a lysate or solution (e.g., homogenate) obtained from the plant host and that contains the protein is contacted with the virus, preferably immobilized on a matrix such as a column, whereby particles of the virus bind (e.g., form complexes) with the protein and separate the protein from the lysate or solution. Then, the protein can be dissociated from the virus.

Another preferred embodiment in accordance with this aspect of the present invention is directed to a method for isolating an endogenous protein from a plant host. The method involves (a) providing a plant virus containing a coat protein, wherein a surface of the coat protein contains a recognition peptide (more preferably one which is non-native to the virus), or in the alternative providing a (recombinant) viral expression vector or pro-vector which upon expression in a cell of the plant host yields particles of the virus. The host is cultured so as to cause production of the protein. The virus particles are caused to come into contact with the protein. This contact is achieved by infecting the host with the virus, introducing the viral expression vector into the host, followed by harvesting the complexes of the virus and protein. Alternatively, a lysate or solution (e.g., homogenate) obtained from the plant host and that contains the protein is contacted with the virus which is preferably immobilized on a matrix such as a column, whereby particles of the virus bind (e.g., form complexes) with the protein, and separate the protein from the lysate or solution. Then, the protein can be dissociated from the virus. A preferred protein is streptavidin.

A further aspect of the present invention is directed to a method of visualizing or localizing a protein or non-proteinaceous small molecule of interest. The method entails (a) providing a virus having affinity for the protein or small molecule and an affinity for a visualization agent; (b) obtaining a host that produces the protein or small molecule of interest; (c) contacting the host or a preparation thereof with the virus; (d) exposing the thus-contacted host or preparation thereof with the visualization agent; and (e) detecting presence or locale of the protein or small molecule.

Yet a further aspect of the present invention is directed to compositions. One such composition is directed to a non-human host containing virus particles having on their surfaces a recognition peptide, the particles having a protein or non-proteinaceous small molecule bound thereto directly or indirectly via the recognition peptide. Another composition is directed to virus particles having on their surfaces a recognition peptide, the particles having a protein or non-proteinaceous small molecule of interest bound thereto directly or indirectly via the recognition peptide. The compositions may further contain a visualization agent such as a detectable label attached to or otherwise associated with the virus (e.g., such as by way of another recognition peptide). These compositions are formed during the course of practicing the methods of the present invention.

The methods and compositions of the present invention take advantage of a virus as an easily programmable and self-replicating biological affinity matrix that can be introduced into a living biological system or an extract thereof, to isolate and purify or otherwise detect, visualize or locate proteins or small molecules, rapidly and inexpensively.

BRIEF DESCRIPTION OF THE DRAWINGS

FIGS. 2A-E are photographs of electrophoretic gels showing purification of streptavidin from total leaf proteins extracted from *Nicotiana benthamiana* using TMVf23 bearing a streptavidin-specific epitope-tag. As a control, wild-type TMV particles were incubated for 3 h in ice with total protein extracts containing premixed streptavidin and centrifuged 10 min. at 14000 rpm. Precipitate contained only some amount of TMV particles (A). Supernatant contained both TMV particles and streptavidin (B). Precipitate of TMVf23 contained also a streptavidin (C). Supernatant in last case did not contain any significant quantities of TMVf23 as well as streptavidin. E—a total protein extracts premixed with streptavidin before incubation with TMV or TMVf23. All electrophoresis conditions are the same as in FIG. 1. Position of streptavidin band is shown by ">".

BEST MODE OF CARRYING OUT INVENTION

The present invention utilizes various properties of viruses for the purposes of purifying or visualizing proteins produced in hosts (which for purposes of this invention is meant to include any biological protein production facility other than a human being). In particular, it utilizes the protein surface of viral particles as a high-affinity ligand and the relatively high molecular weight of virus particles, to develop simple procedures for separation complexes that form between the virus and a protein of interest from other molecules, and in particular separation from proteins and small molecules whose molecular weight is much lower than the weight of the complex of virus and the molecule of interest. Viruses, whether naturally occurring wild-type or mutant viruses, or genetically engineered in nature, are self-replicating "machines" and as such, are very inexpensive. Viruses are also much larger than the great majority of proteins or small molecules for which purification procedures are required. The great difference in weight or in physico-chemical properties can be effectively exploited to separate the molecule of interest from the mixture, such as tissue homogenate, by binding the molecule of interest to a virus particle and then separating the resultant complex from the rest of the mixture. The association between the viral particle and the molecule of interest can later be dissolved in a number of ways known to those skilled in the art of affinity chromatography.

A virus usually has an envelope composed of repeats of one or a small number of so-called coat protein molecules. Thus, the surface of virus is a repetition of monomers displaying polypeptide motifs with very well defined structure. One skilled in the art is able to design a ligand that recognizes a specific viral surface motif and binds to a wild type virus. Such recognition peptide(s) may also be integrated into the viral surface by genetically modifying the coat protein structure of the virus so as to design a specific surface with specific affinity properties. In embodiments of the invention utilizing a virus having more than one coat protein and which require multiple recognition peptides, they may be present on the same or different coat proteins. The site and composition of the recognition peptide(s) are selected so as not to interfere with virus infection, replication, assembly or spreading. Since viruses are usually present in multiple copies in a cell or in purified preparations, they can be used as a natural affinity column.

The invention may be used to purify the proteins or other molecules that are small comparing to the viral particle itself. In the preferred embodiment, the invention is used to separate proteins. In the most preferred embodiment, the invention is used to separate proteins produced by wild-type or genetically engineered or transgenic organisms. For the purposes of the present invention, the virus may be multiplied in a cell that is also the production host, or it may be produced in another organism, in which case the virus and the molecule of interest are then brought into contact such as by mixing homogenates or lysates of the production host (e.g., organism or tissues or cells thereof) with purified/unpurified virus. In one embodiment of the present invention, the virus is engineered to serve both as an expression vector for the protein of interest and as an affinity ligand for that protein. Preferred embodiments entail the use of plant viruses but the method may be practiced with any virus, such as but not limited to, plant virus, animal virus, fungal virus, bacteriophage, or genetically engineered or synthetic replicons having properties described above. Likewise, the method may be practiced using a wide variety of host expression systems including plants (including cell and tissue cultures thereof), animals including non-human animal organisms, and animal and human cell cultures, fungi, bacteria and yeast.

The present method of purifying proteins or small molecules can be practiced in many different ways depending on several factors such as the nature of the protein relative to the host and the manner in which the protein is produced in the host and the nature of the affinity between the virus and the protein. In embodiments where the protein or small molecule is produced endogenously by the host, the method is practiced relatively simply. The host is cultured and lysed. The lysate or a more refined solution containing the protein is contacted with the virus. The virus can be immobilized on a matrix such as a column. Alternatively, the host may be infected by the virus (which might have been propagated in an organism that is not the host) or a viral replication vector such that intact virus particles form in the infected host. Purification of proteins that are not produced endogenously by the host requires a genetic manipulation in order to supply the host with the machinery i.e., at least one transgene that encodes or otherwise directs expression of the protein. In these embodiments, the transgene(s) may be introduced into the host as part of the viral expression/replication vector, or via a separate transformation event. The affinity of the virus for the protein may be direct or indirect in the sense that the transgene may encode the protein in the form of a fusion with a binding peptide that is recognized and bound by the corresponding recognition sequence on the virus.

Beyond these variables, the affinity of the virus for the protein may also be endogenous to the virus or the result of a manipulation of the genetic make-up of the virus (e.g., such as by way of introduction of an epitopic peptide present on the surface of a coat protein of the virus). A preferred way in which to prepare a chimeric virus with which to practice various embodiments of the present invention is as follows. A sequence of short peptide ligand (e.g., generally of from 5 to 12 amino acids in length) with affinity directly to the protein or small molecule of interest is selected. A fusion near the 3'-end part of the coat protein-coding region with the sequence of short peptide ligand is made. TMV particles bearing on the surface epitope tags that are recognized by the corresponding recombinant protein can be produced. Recognition peptides of the present invention are not limited to 5-12 amino acids. They may be longer or even shorter provided that the requisite binding affinity for the protein or small molecule is maintained for the purposes of isolation and purification or visualization and localization.

Groups of plant viruses useful in the practice of the present invention are listed below:

DNA Viruses: Circular dsDNA Viruses: Family: Caulimoviridae, Genus: *Badnavirus*, Type species: commelina yellow mottle virus, Genus: *Caulimovirus*, Type species: cauliflower mosaic virus, Genus "SbCMV-like viruses", Type species: Soybean chloroticmottle virus, Genus "CsVMV-like viruses", Type species: Cassava vein mosaicvirus, Genus "RTBV-like viruses", Type species: Rice tungro bacilliformvirus, Genus: "Petunia vein clearing-like viruses", Type species: *Petunia vein clearing virus;*

Circular ssDNA Viruses: Family: Geminiviridae, Genus: Mastrevirus (Subgroup I Geminivirus), Type species: maize streak virus, Genus: *Curtovirus* (Subgroup II Geminivirus), Type species: beet curly top virus, Genus: *Begomovirus* (Subgroup III Geminivirus), Type species: bean golden mosaic virus;

RNA Viruses:

ssRNA Viruses: Family: Bromoviridae, Genus: *Alfamovirus*, Type species: alfalfa mosaic virus, Genus: *Ilarvirus*, Type species: tobacco streak virus, Genus: *Bromovirus*, Type species: brome mosaic virus, Genus: *Cucumovirus*, Type species: cucumber mosaic virus;

Family: Closteroviridae, Genus: *Closterovirus*, Type species: beet yellows virus, Genus: *Crinivirus*, Type species: Lettuce infectious yellows virus, Family: Comoviridae, Genus: *Comovirus*, Type species: *cowpea mosaic virus*, Genus: *Fabavirus*, Type species: broad bean wilt virus 1, Genus: *Nepovirus*, Type species: tobacco ringspot virus;

Family: Potyviridae, Genus: *Potyvirus*, Type species: potato virus Y, Genus: *Rymovirus*, Type species: ryegrass mosaic virus, Genus: *Bymovirus*, Type species: barley yellow mosaic virus;

Family: Sequiviridae, Genus: *Sequivirus*, Type species: parsnip yellow fleck virus, Genus: *Waikavirus*, Type species: rice tungro spherical virus; Family: Tombusviridae, Genus: *Carnovirus*, Type species: carnation mottle virus, Genus: *Dianthovirus*, Type species: carnation ringspot virus, Genus: *Machlomovirus*, Type species: maize chlorotic mottle virus, Genus: *Necrovirus*, Type species: tobacco necrosis virus, Genus: *Tombusvirus*, Type species: tomato bushy stunt virus, Unassigned Genera of ssRNA viruses, Genus: *Capillovirus*, Type species: apple stem grooving virus;

Genus: *Carlavirus*, Type species: carnation latent virus; Genus: *Enamovirus*, Type species: pea enation mosaic virus, Genus: *Furovirus*, Type species: soil-borne wheat mosaic virus, Genus: *Hordeivirus*, Type species: barley stripe mosaic virus, Genus: *Idaeovirus*, Type species: raspberry bushy dwarf virus;

Genus: *Luteovirus*, Type species: barley yellow dwarf virus; Genus: *Marafivirus*, Type species: maize rayado fino virus; Genus: *Potexvirus*, Type species: potato virus X;

Genus: GOTOBUTTON BM⊥ *Sobemovirus*, Type species: GOTOBUTTON BM_Southern bean mosaic virus, Genus: *Tenuivirus*, Type species: rice stripe virus, Genus: *Tobamovirus*, Type species: tobacco mosaic virus, Genus: *Tobravirus*, Type species: tobacco rattle virus, Genus: *Trichovirus*, Type species: apple chlorotic leaf spot virus; Genus: *Tymovirus*, Type species: turnip yellow mosaik virus; Genus: *Umbravirus*, Type species: carrot mottle virus; Negative ssRNA Viruses: Order: *Mononegavirales*, Family: Rhabdoviridae, Genus: *Cytorhabdovirus*, Type Species: lettuce necrotic yellows virus, Genus: *Nucleorhabdovirus*, Type species: potato yellow dwarf virus;

Negative ssRNA Viruses: Family: Bunyaviridae, Genus: *Tospovirus*, Type species: tomato spotted wilt virus;

dsRNA Viruses: Family: Partitiviridae, Genus: *Alphacryptovirus*, Type species: white clover cryptic virus 1, Genus: *Betacryptovirus*, Type species: "_white clover cryptic virus 2, Family: "_Reoviridae, Genus: *Fijivirus*, Type species: Fiji disease virus, Genus: *Phytoreovirus*, Type species: wound tumor virus, Genus: *Oryzavirus*, Type species: rice ragged stunt virus;

Unassigned Viruses: GenomessDNA: Species banana bunchy top virus, Species coconut foliar decay virus, Species subterranean clover stunt virus, GenomedsDNA, Species cucumber vein yellow virus; GenomedsRNA, Species tobacco stunt virus, GenomessRNA, Species Garlic viruses A,B,C,D, Species grapevine fleck virus, Species maize white line mosaic virus, Species olive latent virus 2, Species ourmia melon virus, Species Pelargonium zonate spot virus;

A variety of animal viruses may also be used. Preferred animal viruses include retro-, adeno-, adeno-associated viruses, herpes simplex virus and baculoviruses. These viruses have been well studied and characterized so as to facilitate genetic engineering of the capsid protein (e.g., to introduce a recognition peptide that directly or indirectly binds the protein or small molecule of interest).

In embodiments where the protein or small molecule is intended for administration to or consumption by a human (or other animal), viruses of plant origin are preferred on account of increased safety and lesser probability of residual contaminating virus in the final product. Such viral systems are well described for different plant hosts (for review see: Porta & Lomonossoff, 1996), insect cell lines, e.g., baculoviral expression systems for insect cells (Reavi et al., 2000), mammalian cells (Colosimo et al., 2000).

A preferred embodiment in accordance with the method entails the production of an exogenous (e.g., heterologous) protein of interest in a plant host (e.g., plant cells, tissue, homogenate or whole plant). The embodiment entails providing a plant virus containing a coat protein, wherein a surface of said coat protein contains a recognition peptide, or providing a viral expression vector or pro-vector which upon processing and infection of a plant yields particles of the virus. Another process step entails genetically modifying e.g., through transient expression or transfection or stable transformation, the plant host to produce the protein of interest. A further process step entails infecting the host with the virus or the viral expression vector pro-vector(s), or otherwise contacting the host or a lysate or solution thereof with the virus, whereby particles of the virus form complexes with the protein of interest via the peptide recognition sequence. Then, particles of the virus having bound thereto the protein are harvested. The protein of interest can then be separated from said virus.

In other preferred embodiments of the invention, the tobacco mosaic virus (TMV) is used to purify to protein made by the plant host. TMV particles consist of 95% coat protein (2130 copies of the coat protein per virion) and about 5% of RNA. The weight of one subunit of coat protein (CP) is 17.5 kd and the size of genomic RNA is 6395 nucleotides. The whole size of the TMV viral particle is about 40000 kd (Creager et al., 1999). It is very easy to isolate TMV using polyethylene glycol precipitation and high-speed centrifugation (Turpen and Reinl, 1998). TMV is a very inexpensive source of protein. In two weeks after inoculation one can harvest from 2 to 10 g of virus per 1 kg of infected tobacco leaves. In general, however, the selection of the virus depends upon the type of host used for the production of the protein (e.g., animal cell, bacterial cell or yeast cell).

In some embodiments, the virus is a bacteriophage having a coat protein containing an oligopeptide that recognizes or binds the protein or small molecule. A phage display system is used to select about a 5-12-mer oligopeptide with high affinity to the virus being used (for example, TMV). Several such systems now are commercially available. Phage display is a selection technique in which a short variable 5-12-mer oligopeptide is inserted into a coat protein of bacteriophage. The sequence encoding this variable oligopeptide is included in the corresponding gene of bacteriophage coat protein. Usually, a 7-mer phage display library has at least $10^9$ independent clones bearing different combinations of 7 amino acids in variable oligopeptides. Phage display has been used to create affinity complexes between a bacteriophage and a protein of interest, allowing rapid identification of peptide ligands for a given target protein by in vitro selection process called "panning" (Parmley & Smith (1988); Cortese et al. (1995)). The phage-protein complex created after panning procedure can be dissociated and a phage with affinity to a target protein can be amplified. Usually, one needs three panning cycles to get bacteriophage with high affinity. After three rounds, individual clones can be characterized by sequencing of variable region in genomic DNA.

Phage display systems have also been developed for identification of small non-proteinaceous molecule binding sites within proteins and are well known in the art. (For a review, see: Rodi et al., 2001; Ehrlich et al., 2000). Such systems have been employed to identify peptides with high affinity to many drugs such as anti-cancer drugs including paclitaxel (e.g., taxol), docetaxel, 2-methoxyestradiol and glycosaminoglycan hyaluronan. For example, the pentapeptide HTPHP (SEQ ID NO: 1) is known to have a high affinity for paclitaxel. See (Rodi et al., 1999). This pentapeptide can be integrated into a viral surface protein as described herein to isolate taxol from taxol-producing plant tissues. Therapeutic agents and herbicides are examples of such small molecules. In general, any non-peptidic organic molecule produced by a host such as a plant, animal, bacterial or yeast cell, and that is recognizable (e.g., has a binding affinity for) a peptide may be isolated or detected in accordance with the present invention. Peptides that bind these molecules may also be identified using phage display. In general, the small molecules have molecular weights of from about 250 daltons to about 1,000 daltons.

The virus can be caused to come into contact and bind the protein in the intact host (e.g., in vivo), such as by infecting the host with the virus or a viral expression vector. Alternatively, the virus may be contacted with the protein external to the confines of the host e.g., once the protein is contained in an homogenate or lysate, such as by affinity chromatography with viral particles absorbed onto a matrix such as a column. The conditions employed for dissociating the virus from the protein (or small molecule) depend on the specific type of interactions and can be created by varying physico-chemical parameters e.g., pH; temperature; ions, chelating agents concentration, etc. Selecting appropriate conditions will be within the level of skill in the art of protein purification. See, Kent, 1999; Gurgel et al., 2000; Wilchek & Chaiken, 2000; Muronetz et al., 2001). Ultrafiltration is one such way of separating protein from virus. In embodiments where the protein is expressed in the form of a fusion with an affinity peptide that binds the recognition peptide on the surface of the virus, separation of the protein is facilitated by the presence of a cleavable linkage between the protein and its fusion partner. The cleavage sites can be but not limited to those recognized by enterokinase (Choi et al., 2001) or cyanogen bromide (Assadi-Porter et al., 2000). Examples of other cleavage sites are trypsin, chymotrypsin, factor Xa protease and hydroxylamine. Yet another manner of creating a cleavable fusion with the protein of interest is based on the use of inteins. See, Chong et al. (1997). This system utilizes a protein-splicing element termed an intein from yeast in conjunction with an affinity tag. The modified intein can be induced to undergo self-cleavage at its N-terminal peptide linkage under certain mild chemical conditions. A target protein is cloned in-frame with the N-terminus of the intein-affinity tag fusion. The immobilized fusion protein is then induced to undergo self-cleavage under mild conditions (which does not require proteolytic cleavage), resulting in the release of the target protein while the intein-affinity tag remains bound to a column (Cantor & Chang, 2001). Thus, in the present invention, the transgene introduced into the host expresses the protein in the form of a fusion with an intein based cleavable affinity tags that bind to the viral surface.

This invention is suitable for the purification of transgenic and endogenous proteins alike as well as non-proteinaceous molecules occurring naturally or as a consequence of transgene expression in wide variety of hosts including but not limited to members of the plant, animal and bacterial kingdoms. Examples of such proteins can be, but not limited to pharmaceutically and industrially important proteins, e.g. immune response proteins, enzymes including DNA modifying enzymes, starch-, cell wall modifying enzymes, proteases, lipases etc.

In the case of proteins or small molecules that are exogenous to the host, transgenes encoding the protein (by itself or in the form of a fusion with a peptide that binds the recognition peptide on the virus) or the expression of which result in the production of the small molecule, are introduced into a non-human host in accordance with standard techniques. In general, these techniques include stable or transient transformation or by way of viral delivery (e.g., infection of the cell by the viral expression vector). Methods of creating transgenic organisms with stably integrated foreign genes are well described in the literature. For example, DNA can be transformed into plant cells via *Agrobacterium*-mediated delivery. See, U.S. Pat. Nos.: 5,591,616; 4,940,838; and 5,464,763. Other methods include particle or microprojectile bombardment (U.S. Pat. No. 5,100,792; European Patent (EP) 444,882 B1; EP 434,616 B1), microinjection (WO 09209696; WO 09400583 A1; EP 175,966 B1) and electroporation (EP 564,595 B1; EP 290,395 B1; WO 08706614 A1). Procedures of transgene delivery into animal, bacterial and yeast cells are well established. A popular method of transgene delivery into animal cells is retrovirus-mediated (Robbins & Givizzani, 1998; Reynolds et al., 1999). Other methods with synthetic (non-viral) carriers are also suitable (for review see: Bown et al., 2001). Transformation methods for yeast and bacterial cells are well described in many manuals e.g., *Yeast Protocol Handbook* (2000) and Sambrook et al., (1989).

The present invention is amenable to industrial application and scaling-up because it can accommodate techniques such as tissue homogenization, centrifugation and ultrafiltration. It can be applied to production of proteins and small molecules in any prokaryotic or eukaryotic system. Thus, the invention will allow development of a universal, inexpensive and easily scale-up method of purification of any protein of interest from any kind of prokaryotic or eukaryotic system designed for protein production.

The use of viral particles provides an inexpensive source of homogenous protein (coat protein), which at the same time is easily genetically modified. Another key advantage of this invention is the ability to use epitopes to identify an oligopeptide with high affinity to the target protein. By incorporating the epitope into the viral coat protein as the surrogate affinity matrix fusion, the protein or small molecule of interest may be isolated without any modification and without the need for any subsequent cleavage step. As result, an intact protein of interest is produced. The fact that viral particles are significantly larger than even the largest protein (about 40000 kD vs. a maximum 300 kD), allows efficient separation of the protein of interest from the viral particles by simple ultrafiltration.

The virus purification tag systems of the present invention are also used for localization or detection of proteins on the surface or in different compartments of cells. Immunostaining with gold-labeled antibody is widely applied for solution of such experimental tasks (Milne RG, 1993). Another approach in this field is the use of gold-labeled streptavidin (Prendes et al., 1999). The method of the present invention entails visualizing or localizing a protein or non-proteinaceous small molecule of interest, comprising: (a) providing a virus having affinity for the protein or small molecule and an affinity for a visualization agent; (b) obtaining a host that produces the protein or small molecule of interest; (c) contacting the host or a preparation thereof with the virus;

(d) exposing the thus-contacted host or preparation thereof with the visualization agent; and (e) detecting presence or locale of the protein or small molecule. In this aspect of the present invention, the virus functions as a matrix providing a large number of interaction sites for amplification of a signal that can be detected by standard techniques such as immunological-based methods (e.g., ELISA) and electron microscopy (e.g. labeling with gold). Selecting naturally occurring viruses or genetically engineering viruses that recognize or bind various proteins or small molecules are well within the level of skill in the art. In addition, chimeric viruses can be made that recognize both the protein/small molecule and a visualization agent. For example, chimeric TMV particles are produced by in vitro self-assembly. To localize a protein in a host (e.g., a cell surface protein), a phage display system is used to identify an epitope tag such as a heptapeptide that recognizes that protein. A fused TMV CP (coat protein) containing this epitope tag near the carboxyl end of the protein is then created. The virus is further engineered to contain a CP-bearing epitope tag recognizing streptavidin such that when self-assembled in vitro, chimeric virus protein particles bearing both epitope tags are generated. To localize the position of the protein, the chimeric self-assembled TMV particles are combined with the host as is done in accordance with techniques involving antibodies described in the prior art. The cell-TMV complex is then incubated with a detectably labeled (e.g., gold-labeled) streptavidin. Electron microscope analysis shows localization of the protein by both very specific rod-shaped TMV particles and black spots of gold-label. Plainly, a variety of visualization or localization agents e.g., detectable labels and physical agents (e.g., ultraviolet light, fluorescent agents, enzymatic activity causing substrate visualization—identical to those being used in Western blot systems) may be used depending on the detection mechanism employed.

EXAMPLES

The examples provided below demonstrate that infection of a host by a TMV viral expression vector yielded particles of a virus containing a streptavidin recognition peptide sequence (epitope) on the surface of CP. The site and composition of streptavidin recognition peptide sequence did not interfere significantly with virus infection, replication, assembly or spreading. After inoculation of healthy young *N. benthamiana* plants with in vitro transcribed RNA, virus particles with engineered affinity tag to streptavidin were obtained.

Experiments with commercial streptavidin demonstrated high affinity interaction of TMVf23 particles with streptavidin that enabled isolation and purification of streptavidin from its original concentration (100 mkg per 1 g of leaf tissue) using just one cycle of purification. TMVf23-streptavidin complex was dissociated at mild conditions and streptavidin was separated from TMVf23 by ultrafiltration.

Example 1

Preparation of Infectious TMV with a Modified Coat Protein

We used cDNA copy of TMV inserted into pBR322 plasmid known as TMV304, originated from laboratory of Dr. J. Culver. 937bp KpnI-NcoI fragment with 3'-end of TMV (including full coat protein (CP) sequence) was cut out from TMV304 and inserted into plCxxxx vector (a modified SK vector with additional restriction sites, including NcoI). This produced the plasmid plCyyyy (TMVcp3). The 21-nucleotide sequence encoding the heptapeptide TLIAHPQ (SEQ ID NO: 7) that has affinity to streptavidin (Delvin et al., 1990; Lam et al., 1991) was inserted into the gene for the TMV CP by POR-site-specific mutagenesis. We incubated plCyyyy with two combinations of primers:

```
                                    (SEQ ID NO:2)
1) Forward 24-mer Bluescript primer:
(5'-CGCCAGGGTTTTCCCAGTCACGAC-3') and (SEQ ID NO:3)
cpfR 47-mer primer:
(5'-TTGGGGATGCGCGATCAATGTGGAAGTCCAAA

CCAAACCAGAAGAGC-3').

(SEQ ID NO:4)
With:
Reverse 24-mer Bluescript primer:
(5'-AGCGGATAACAATTTCACACAGGA-3') and (SEQ ID NO:5)
cpfF 46-mer primer:
(5'-ACATTGATCGGCCATCCCCAAGGTCCTGCAAC

TTGAGGTAGTCAAG-3').
```

The PCR reaction was conducted with Pfu Turbo DNA Polymerase (Stratagene). Two homogenous PCR products were purified by Qiagen PCR-purification kit, mixed, denaturated, renaturated, and incubated with forward and reverse Bluescript primers, and Pfu Turbo DNA polymerase. Final homogenous PCR product was digested with KpnI and NcoI restriction enzymes and inserted into plCxxxx vector. Correctness of mutagenized sequence was confirmed by sequencing. This resulted in the fused TMVf23 coat protein having the following sequence: 5'

(SEQ ID NO:6)
MetSYSITTPSQFVFLSSAWADPIELINLCTNALGNQFQTQQARTVVQRQ

FSEVWKPSPQVTVRFPDSDFKVYRYNAVLDPLVTALLGAFDTRNRIIEVE

NQANPTTAETLDATRRVDDATVAIRSAINNLIVELIRGTGSYNRSSFESS

SGLVWTS<u>TLIAHPQ</u>GPATstop 3'

(streptavidin epitope-tag sequence is underlined).

The modified CP gene was inserted back into plasmid TMV304 resulting in the recombinant DNA plCzzzz. Infectious RNA copy of modified virus (designated TMVf23) was transcribed in vitro according to Turpen and Reinl (1998) and inoculated into young plants of *Nicotiana benthamiana*. First symptoms of infection both for TMV and TMVf23 appeared 5-6 days after inoculation. TMV caused very severe symptoms while for TMVf23 symptoms were milder but also very well evident. Two weeks after inoculation virus was isolated both from TMV and TMVf23 inoculated plants. Recovery of TMV and TMVf23 was very good with both yielding 2 mg of virus per 1 g of leaf tissue. The fused nature of CP from TMVf23 was demonstrated by electrophoresis in PAGE (FIG. 1) by the reduced mobility (indicating increased size) of TMVf23.

Example 2

Purification of Streptavidin with Modified CP from TMV

Figure 1:
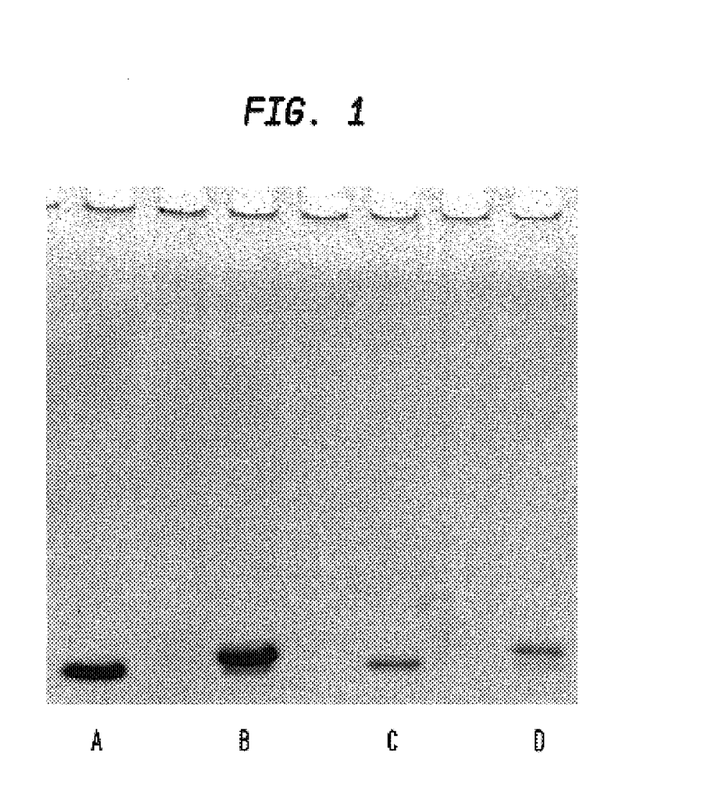
FIGS. 1A, 1B, 1C and 1D are photographs of electrophoretic gels showing a comparative analysis of coat proteins from wild-type TMV and TMVf23. Viral particles were incubated for 5 minutes at 95° C. and immediately after that loaded on the 10-20% linear gradient SDS-Tris-glycine PAGE. A—6 μg and C—0.6 μg of unmodified TMV. B—6 μg and D—0.6 μg of TMVf23. Gel was stained in Coomassie blue.
Figure 2:
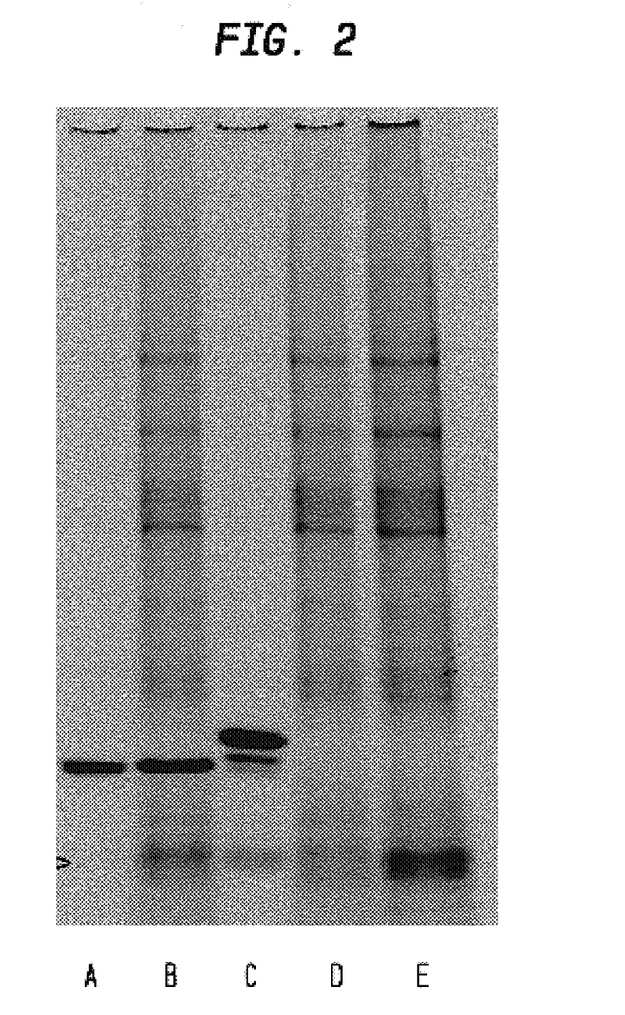

TMV particles with fused CP-tag were tested for affinity to commercial streptavidin. Several grams of *N. benthamiana* leaves were homogenized with liquid nitrogen. After that, equal volume (1 g/1 ml) of extraction buffer was added (50 mM tris-HCl, pH8.0; 0.5M NaCl; 0.25% Nonidet P-40; 1.3% polyvinylpolypyrrolidone (PVPP); 1 mM phenylmethylsulfonylfluoride (PMSF); 3 mkg/ml pepstatin; 1 mkg/ml leupeptin; 5 mM ascorbic acid) as well as streptavidin equivalent to 100 μg per 1 g of leaf tissue. All manipulations were conducted at 0 to 4° C. Homogenate was centrifuged 2 min. at 14000 rpm and the resulting supernatant was centrifuged 2 times for 10 min. at 14000 rpm. The supernatant was adjusted to 25% $(NH_4)_2SO_4$ and centrifuged 10 min. at 14000 rpm. The 25% $(NH_4)_2SO_4$ supernatant was adjusted to saturated $(NH_4)_2SO_4$ and centrifuged 10 min. at 14000 rpm. Precipitate was suspended in 10 mM phosphate buffer, pH7.2, clarified by centrifugation and incubated with 1 mg of TMVf23 per 1 g of leaf tissue for 3 h in ice. Suspension was centrifuged 10 min. at 14000 rpm. Pellet was suspended in 10 mM phosphate buffer and analyzed by polyacrylarmide gel (PAGE). Streptavidin was found significantly purified from mixture of plant proteins (FIG. 2).

Figure 3:
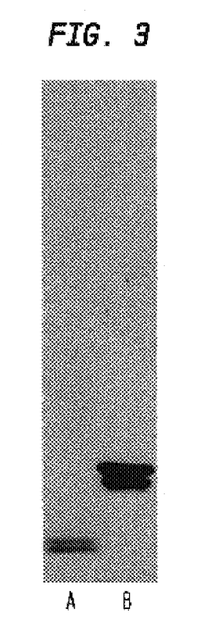
FIG. 3 is a photograph of an electrophoretic gel showing separation of the complex TMVf23-streptavidin. Electrophoresis conditions are the same as in FIG. 1.

Dissociation of the TMVf23-streptavidin complex was next optimized. It was found that the most optimal and efficient method to dissociate streptavidin from TMVf23 was to suspend the TMVf23-streptavidin complex in 0.2M acetic acid, pH4.6 and centrifuge it in Centricon™ filters (Nanosep 300K). Streptavidin was quantitatively passed through the filter (FIG. 4A) and TMVf23 was quantitatively left on the filter (FIG. 3B).

Example 3

Identification of a Heptapeptide Recognizing Wild-Type TMV Coat Protein

Using phage display system, we determined a heptapeptide sequence recognizing intact wild-type TMV particles. This sequence was used for construction of cassette: ATG-heptapeptide sequence-enterokinase cleavage site. Cassette sequence was fused with the gene of hepatitis B S protein. Fused construct was inserted into crTMV viral delivery vector and expressed in plants.

Example 4

Use of TMVf23 and Streptavidin in Protein Detection

TMV as well as F23 particles were adsorbed to grids by "co-cultivation on the drop" for 15 min at room temperature. To reduce background, grids were treated with 1% BSA in 0.1M phosphate buffer, pH 7.2, for 1 h at room temperature. Grids were incubated with gold-labeled streptavidin (Sigma) overnight at 4° C. followed by washing in 1% BSA in phosphate buffer, and water, and analyzed via electron microscopy. FIGS. 2A and B show TMV particles treated with gold-labeled streptavidin. No specific interaction between streptavidin and TMV was found. FIGS. 2C, D and E show F23 particles treated in the same way. In this case, clear affinity between gold-labeled streptavidin and F23 particles can be seen.

Example 5

Purification of Streptavidin from *Streptomyces Avidinii*

Figure 4A:
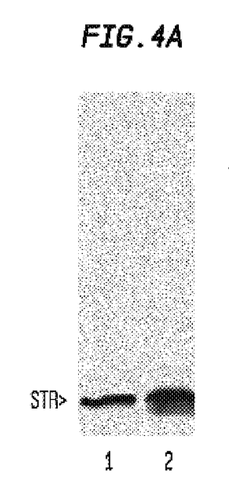
FIG. 4A is a photograph of a Western blot and FIG. 4B is a photograph of an SDS PAGE (B) analysis of streptavidin isolated and purified from *Streptomyces avidinii* and stained by Bio-Safe Coomassie (Bio-Rad). A1—1 mkl of secreted streptavidin (about 50 ng); A2—100 ng of commercial streptavidin (Sigma). B1—500 ng of secreted nonpurified streptavidin. B2—equal amount of streptavidin after purification with F23. B3—1 mkg of commercial streptavidin (Sigma).
Figure 4B:
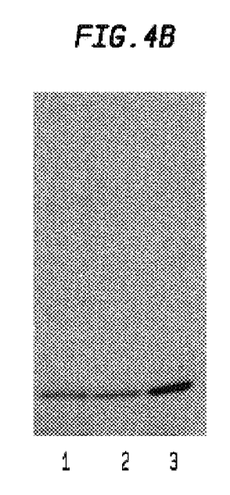

TMV-based purification tags can also be used for protein purification in bacterial and animal biotechnology. To demonstrate this, streptavidin was purified from a naturally occurring, commercial source—*Streptomyces avidinii*. *S. avidinii* cells were grown in synthetic media. The bacteria were cultured for 7 days, and then harvested and centrifuged for 5 min at 12000×g. Supernatant containing streptavidin (FIG. 4 A, lane 1) was precipitated with 80% ammonium sulfate and left overnight at 4° C. Protein was precipitated by centrifugation for 10 min at 12000×g and dissolved in 10 mM phosphate buffer (0.1 of original volume). Total protein solution was mixed with F23 in proportion 1:10 and left for 1 h in ice. Streptavidin-F23 aggregates were precipitated by centrifugation and dissociated with 0.2M acetic acid, pH 3.5. Streptavidin was separated from F23 by centrifugation through NANOSEP 300K (FIG. 4B). The yield of purified streptavidin was around 90%.

Streptavidin isolated from *Streptomyces avidinii* formed stronger complex with F23 compared to commercially available samples. (Dissociation at pH 4.6 was adequate for the commercial samples.) Relatively milder conditions of streptavidin purification were used compared to a commercial purification procedure. Thus, the present invention enables isolation of a more intact and, as result, more active form of streptavidin.

CITATIONS OF LITERATURE REFERENCED IN APPLICATION

1. Assadi-Porter et al., Arch. Biochem. Biophys. 376(2): 252-8 (2000)
2. Boyer et al., Virology 198:415-426 (1994).
3. Bown et al., Int. J. Pharmaceutics 229:1-21 (2001).
4. Cantor & Chang, Protein Expr. Purif. 22(1):135-40 (2001).
5. Choi et al., Biotechnol. Bioeng. 75(6):718-24 (2001).
6. Chong et al., Gene 192:271-281 (1997).
7. Colosimo et al., Biotechniques 29(2):314-24 (2000).
8. Cortese, et al., Curr. Opin. Biotechnol. 6(1):73-80 (1995).
9. Creager, et al., Plant Cell. 11(3):301-8 (1999).
10. Devlin et al., Science 249(4967):404-6 (1990).
11. Ehrlich et al., Methods Mol. Biol. 147:209-20 (2000).
12. Fischer et al., Biotechnol Appl. Biochem. 30:101-108 (1999).
13. Fischer et al., Biotechnol Appl. Biochem. 30:113-116 (1999).
14. Fitchen et al., Vaccine 13(12):1051-7 (1995).
15. Gurgel, Carbonell & Swaisgood, Bioseparation 9(6): 385-92 (2000).
16. Hamamoto, Bio/Technology 11:930-932 (1993).
17. Johnson et al., Annu. Rev. Phytopathol. 35: 67-86 (1997).
18. Kent, UM, Methods Mol. Biol. 115:23-8 (1999)
19. Koo et al., Proc Natl Acad Sci USA 96(14):7774-9 (1999).
20. Kumagai et al., Proc. Natl. Acad. Sci. USA 90:427-430 (1993).
21. Lam et al., Nature 354(6348):82-4(1991).
22. McLain, AIDS Res Hum Retroviruses. 11(3):327-34 (1995).
23. Milne, Electron microscopy of in vitro preparations. In: Diagnosis of Plant Virus Diseases. Ed. By R. E. F. Matthews. CRC Press, 1993
24. Muronetz, Sholukh & Korpela, J. Biochem. Biophys. Methods 49 (1-3):29-47 (2001).
25. Parmely et al., Gene 73(2):305-18 (1988).
26. Porta & Lomonossoff, Mol. Biotechnol. 5(3):209-221 (1996).
27. Prendes et al., Blood 94(4): 1300-12 (1999).
28. Reavi et al., Protein Expr Purif. 18(2):221-8 (2000).
29. Reynolds et al., Molec. Medicine Today 5:25-31 (1999)
30. Robbins & Ghivizzani, Pharmacology & Therapeutics 80(1):35-47 (1998)
31. Rodi et al., J. Mol. Biol. 285:197-203 (1999).
32. Rodi et al., Comb. Chem. High Throughput Screen 7:553-72 (2001)
33. Sambrook et al., Molecular Cloning: a laboratory manual. Cold Spring Harbor Laboratory Press, Cold Spring Harbor, N.Y. (1989)
34. Shivprasad et al., Virology 255:312-323 (1999).
35. Spitsin et al., Proc. Natl. Acad. Sci. USA 96:2549-53 (1999).
36. Turpen et al., *Tobamovirus* vectors for expression of recombinant genes in plants. Methods in biotechnology 3. Recombinant proteins in plants: Production and isolation of clinically useful compounds, edited by C. Cunningham and A. J. R. Porter, 1998, Humana Press Inc.
37. Yeast Protocol Handbook, Clontech Laboratories, Inc. (2000).
38. Yusibov et al., Proc. Natl. Acad. Sci. USA 94(11): 5784-8 (1997).
39. Wilchek & Chaiken, Methods Mol. Biol. 147:1-6 (2000).

INDUSTRIAL APPLICABILITY

The present invention is useful in the fields of protein and small molecule purification, and in the manufacturing of commercially useful organic molecules.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

The invention claimed is:

1. A method of purifying a protein or non-proteinaceous small molecule of interest, comprising:
   (a) providing a plant virus having on its surface at least one recognition peptide, or preparing a plant viral expression vector which upon infection of an organism yields particles of the virus, wherein said virus or viral expression vector is genetically modified to produce said recognition peptide;
   (b) obtaining a host that produces the protein or small molecule of interest independent from or due to presence of the virus therein; and
   (c) infecting the host with the virus or the viral expression vector whereby particles of the virus form complexes with the protein or small molecule via the peptide recognition sequence, followed by harvesting the complexes of the virus and protein from the host, or contacting a lysate or solution of the host with the virus, whereby particles of the virus form complexes with the protein or small molecule via the peptide recognition sequence, and the protein or small molecule is separated from the solution.

2. The method of claim 1 further comprising (d) separating the protein or small molecule of interest from the virus particles.

3. The method of claim 1 wherein said recognition peptide is a FLAG polypeptide or a polyhistidine polypeptide, and said protein of interest is fused to an affinity peptide that binds said recognition peptide.

4. The method of claim 3 wherein said affinity peptide comprises a single-chain fragment (scFv) of an antibody or an antibody that binds said FLAG polypeptide or said polyhistidine polypeptide.

5. The method of claim 1 wherein said recognition peptide is an affinity peptide, a single-chain fragment (scFv) of an antibody, or an antibody that binds a small non-proteinaceous molecule.

6. The method of claim 1, wherein said recognition peptide is a polypeptide sequence introduced into a coat protein of the virus and has an affinity to said protein of interest.

7. The method of claim 1 wherein (a) comprises preparing a viral expression vector that contains a transgene encoding the protein of interest or another protein, the production of which results in production of the protein or small molecule of interest in the host.

8. The method of claim 1 wherein (b) comprises transforming the host with a transgene encoding the protein or another protein the production of which results in production of the protein or small molecule of interest.

9. The method of claim 8 wherein said transgene encodes a fusion protein comprising the protein of interest linked via a cleavable linkage to an affinity peptide that binds the recognition peptide.

10. The method of claim 9 wherein the cleavable linkage comprises an enterokinase site.

11. The method of claim 9 wherein the cleavable linkage comprises a cyanogen bromide-sensitive site.

12. The method of claim 9 wherein the cleavable linkage comprises a cleavable intein or a fragment thereof.

13. The method of claim 1 wherein the virus is tobacco mosaic virus.

14. The method of claim 1 wherein the host is a plant cell, a plant tissue or a plant.

15. The method of claim 1 wherein the surface of the virus contains more than one recognition peptide having the same or different affinities.

16. A method of production and purifying a protein of interest, comprising:
   (a) providing a plant virus containing a coat protein, wherein a surface of said coat protein contains a recognition peptide, or providing a viral expression vector or pro-vector which upon processing and infection of a plant yields particles of the virus, wherein said virus or viral expression vector is genetically modified to produce said recognition peptide;
   (b) genetically modifying a plant host to produce the protein of interest; and
   (c) infecting the host with the virus or the viral expression vector whereby particles of the virus form complexes with the protein via the peptide recognition sequence, followed by harvesting the complexes of the virus and protein from the plant host, or contacting a lysate or solution of the plant host with the virus, whereby particles of the virus form complexes with the protein or small molecule via the peptide recognition sequence, and the protein or small molecule is separated from the solution.

17. The method of claim 16 further comprising (d) separating said protein of interest from said virus.

18. The method of claim 16 further comprising (d) separating the protein interest from the virus particles.

19. The method of claim 16 wherein said recognition peptide is a FLAG polypeptide or a polyhistidine polypeptide, and said protein of interest is fused to an affinity peptide that binds said recognition peptide.

20. The method of claim 19 wherein said affinity peptide comprises a single-chain fragment (scFv) of an antibody or an antibody that binds said FLAG polypeptide or said polyhistidine polypeptide.

21. The method of claim 16 wherein said recognition peptide is an affinity peptide, a single-chain fragment (scFv) of an antibody, or an antibody that binds the protein of interest.

22. The method of claim 16 wherein (a) comprises preparing a viral expression vector or pro-vector which upon processing and infection of a plant yields particles of the virus, wherein said virus or viral expression vector is genetically modified to produce said recognition peptide.

23. The method of claim 16 wherein said protein of interest is part of a fusion protein and is linked via a cleavable linkage to an affinity peptide that binds the recognition peptide.

24. The method of claim 23 wherein said cleavable linkage comprises a site selected from the group consisting of cleavable intein or a fragment thereof; an enterokinase site; and a cyanogen bromide-sensitive site.

25. The method of claim 16 wherein the virus is tobacco mosaic virus.

26. The method of claim 16 wherein the plant host is a plant cell, a plant tissue or a plant.

27. The method of claim 16 wherein the surface of the virus contains more than one recognition peptide having the same or different affinities.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      pentapeptide

<400> SEQUENCE: 1

His Thr Pro His Pro
 1               5

<210> SEQ ID NO 2
<211> LENGTH: 24
<212> TYPE: DNA
```

```
<213> ORGANISM: Artificial Sequence
<220> FEATURE:
<223> OTHER INFORMATION: Description of Artificial Sequence: Primer

<400> SEQUENCE: 2
cgccagggtt ttcccagtca cgac                                          24

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 3
ttggggatgc gcgatcaatg tggaagtcca aaccaaacca gaagagc                 47

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
agcggataac aatttcacac agga                                          24

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 5
acattgatcg cgcatcccca aggtcctgca acttgaggta gtcaag                  46

<210> SEQ ID NO 6
<211> LENGTH: 166
<212> TYPE: PRT
<213> ORGANISM: Tobacco mosaic virus

<400> SEQUENCE: 6

Met Ser Tyr Ser Ile Thr Thr Pro Ser Gln Phe Val Phe Leu Ser Ser
  1               5                  10                  15

Ala Trp Ala Asp Pro Ile Glu Leu Ile Asn Leu Cys Thr Asn Ala Leu
                 20                  25                  30

Gly Asn Gln Phe Gln Thr Gln Gln Ala Arg Thr Val Val Gln Arg Gln
             35                  40                  45

Phe Ser Glu Val Trp Lys Pro Ser Pro Gln Val Thr Val Arg Phe Pro
     50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
                 85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
    130                 135                 140
```

```
                                    -continued

Phe Glu Ser Ser Ser Gly Leu Val Trp Thr Ser Thr Leu Ile Ala His
145                 150                 155                 160

Pro Gln Gly Pro Ala Thr
                165

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      heptapeptide

<400> SEQUENCE: 7

Thr Leu Ile Ala His Pro Gln
  1               5
```